United States Patent

Lartey et al.

Patent Number: 5,834,438
Date of Patent: Nov. 10, 1998

[54] 4"-DEOXYERYTHROMYCIN DERIVATIVES

[75] Inventors: Paul A. Lartey, Wadsworth; Larry L. Klein; Ramin Faghih, both of Lake Forest; Hugh N. Nellans, Mundelein, all of Ill.

[73] Assignee: Abbott Laboratories, Abbott Park, Ill.

[21] Appl. No.: 435,903

[22] Filed: May 4, 1995

Related U.S. Application Data

[62] Division of Ser. No. 284,730, Aug. 2, 1994, Pat. No. 5,578,579, which is a continuation of Ser. No. 944,150, Sep. 11, 1992, abandoned, which is a continuation-in-part of Ser. No. 823,490, Jan. 21, 1992, abandoned.

[51] Int. Cl.[6] .................................................. A61K 31/70
[52] U.S. Cl. .............................. 514/29; 536/7.2; 536/7.4
[58] Field of Search ................................ 514/29; 536/7.2, 536/7.4

[56] References Cited

U.S. PATENT DOCUMENTS

| | | |
|---|---|---|
| 4,640,910 | 2/1987 | Faubl et al. . |
| 4,677,097 | 6/1987 | Omura et al. . |
| 4,681,872 | 7/1987 | Freiberg et al. . |
| 4,833,236 | 5/1989 | Morimoto et al. . |
| 4,948,782 | 8/1990 | Omura et al. . |
| 5,175,150 | 12/1992 | Omura et al. .............................. 514/29 |

FOREIGN PATENT DOCUMENTS

| | | |
|---|---|---|
| 213 617 | 3/1987 | European Pat. Off. . |
| 215 355 | 3/1987 | European Pat. Off. . |
| 349 100 | 1/1990 | European Pat. Off. . |

OTHER PUBLICATIONS

Sunazuka, et al., *Chem. Pharm. Bulletin*, 37(10): 2701–2709 (1989).

*Primary Examiner*—Elli Peselev
*Attorney, Agent, or Firm*—Mona Anand

[57] ABSTRACT

4"-Deoxy derivatives of erythromycin having the Formula (I)

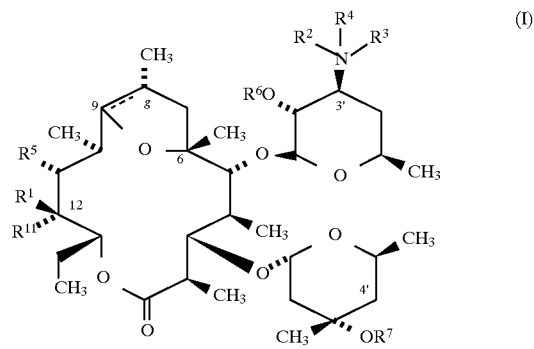

and pharmaceutically acceptable salts thereof, which are enhancers of gastric motility but have minimal antibacterial activity, as well as pharmaceutical compositions containing the same and methods for their use and preparation.

9 Claims, No Drawings

4"-DEOXYERYTHROMYCIN DERIVATIVES

This application is a divisional of U.S. Ser. No. 08/284,730, filed Aug. 2, 1994, now U.S. Pat. No. 5,578,579, which is a continuation of U.S. Ser. No. 07/944,150, filed on Sep. 11, 1992, now abandoned, which is a continuation-in-part of U.S. Ser. No. 07/823,490, filed Jan. 21, 1992, now abandoned.

TECHNICAL FIELD

This invention relates to novel 4"-deoxyerythromycin derivatives of erythromycins A and B and pharmaceutical compositions containing these compounds, as well as the use thereof in treating gastrointestinal disorders and in facilitating the placement of diagnostic and therapeutic instrumentation into the proximal small intestine. The invention also relates to synthetic intermediates employed therein.

BACKGROUND OF THE INVENTION

The primary function of the alimentary or gastrointestinal (GI) tract is to provide the body with a balanced supply of water, electrolytes and nutrients. In order for this to be achieved, food must be moved along the GI tract at an appropriate rate for digestion, absorption and secretion to take place. Food is normally transported through the GI tract in a well-coordinated manner by propulsive movements which are mediated by clusters of smooth muscle contractions known as migrating myoelectric complexes, in a process commonly referred to as peristalsis.

Defects in the normal motility pattern can lead to the development of chronic, painful and debilitating disorders. For example, an incompetent or weak lower esophageal sphincter may result in frequent reflux of ingested food from the stomach into the esophagus which may lead to esophagitis. Prokinetic agents (also called motility-enhancing agents) are useful in treating reflux esophagitis because they (a) increase the pressure of the lower esophageal sphincter, thereby inhibiting reflux; (b) increase the force of esophageal peristalsis to facilitate clearance of food from the esophagus into the stomach; and (c) increase gastric emptying, thereby further decreasing the mass available for reflux.

There is a need, however, for improved prokinetic agents in the treatment of this disorder. Presently used cholinergic drugs such as bethanechol and dopamine receptor blocking agents such as metoclopramide may exhibit serious disadvantages. Bethanechol, for example, should be avoided by elderly patients while metoclopramide has a narrow therapeutic index, pronounced central nervous system (CNS) side effects and is known to stimulate prolactin release.

Patients suffering from other GI motility-related disorders such as delayed gastric emptying, diabetic gastroparesis, anorexia, gall bladder stasis, surgically induced adynamic ileus and chronic constipation (colonic inertia) may also benefit from treatment with prokinetic agents. In addition, prokinetic agents can aid in the placement of diagnostic and therapeutic instrumentation, such as during the insertion of enteral feeding tubes into the proximal small intestine.

Another, less common but very painful and disruptive GI motility disorder is chronic intestinal pseudoobstruction. Patients who are severely afflicted with this problem cannot tolerate oral feedings and require total parenteral nutrition. Metochlopramide and bethanechol are also used in the treatment of this disorder but often with disappointing results. Prokinetic agents could not only be useful in alleviating the distress associated with this disorder, but also in severe cases could be used to facilitate treatment by decompression of the upper GI tract by nasogastric tubal aspiration. Increased gastric motility brought about by the use of a prokinetic agent has been shown to facilitate the placement of the necessary tubes into the intestine.

Macrocyclic lactone (macrolide) prokinetic agents are known. For example, J. S. Gidda et al., in European Patent Application No. 0349100, published Jan. 3, 1990, disclose 12-membered macrolides for use as gastrointestinal motility enhancers. S. Omura and Z. Itoh, in U.S. Pat. No. 4,677,097, issued Jun. 30, 1987, European Application No. 215,355, published Mar. 25, 1987, and European Application No. 213,617, published Mar. 11, 1987, disclose derivatives of erythromycins A, B, C and D which are useful as stimulants of digestive tract contractile motion. Additionally, T. Sunazuka, et al., Chem. Pharm. Bull. 37(10): 2701–2709 (1989) discloses quaternary derivatives of 8,9-anhydroerythromycin A 6,9-hemiacetal and 9,9-dihydroerythromycin A 6,9-epoxide with gastrointestinal motor stimulating activity. However, none of these references disclose 4"-deoxyerythromycin derivatives; thus, the compounds of these references are distinct from those of the present invention, in which novel N-substituted derivatives of 4"-deoxyerythromycin are disclosed which possess an unexpected degree of prokinetic activity.

4"-Deoxy derivatives of erythromycin are described as antibacterial agents by S. Morimoto et al., in U.S. Pat. No. 4,833,236, issued May 23, 1989; H. Faubl et al., in U.S. Pat. No. 4,640,910, issued Feb. 3, 1987; and L. A. Freiberg et al., in U.S. Pat. No. 4,681,872 issued Jul. 21,1987. These references do not suggest that 4"-deoxyerythromycin derivatives have prokinetic activity. It has now been found that N-substituted derivatives of 4"-deoxyerythromycin have a high degree of prokinetic activity. This finding has enabled a therapeutically useful agent having diminished potential side-effects to be produced.

SUMMARY OF THE INVENTION

In one aspect of the present invention are provided macrocylic prokinetic agents of Formula (I)

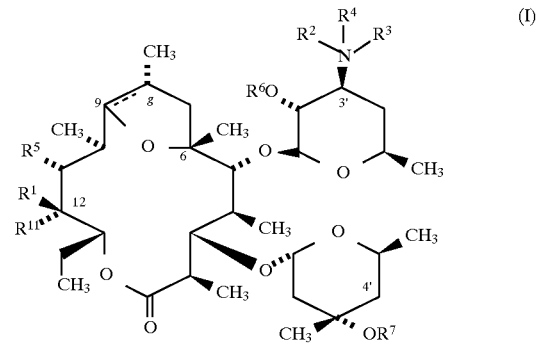

and pharmaceutically acceptable salts thereof, wherein the dotted line is an optional second C8-to-C9 bond.

In Formula (I), one of $R^1$ and $R^{11}$ is hydrogen and the other is methyl. Alternatively, $R^{11}$ is methyl and $R^1$ is hydroxy or, taken together with $R^5$ and the carbons to which they are attached, $R^1$ forms a cyclic carbonate.

$R^2$ and $R^3$ in Formula (I) are independently selected from the group consisting of hydrogen, loweralkyl, halo-substituted loweralkyl, cyano-substituted loweralkyl, hydroxy-substituted loweralkyl, amino-substituted loweralkyl, loweralkenyl, loweralkynyl, lower cycloalkyl, lower cycloalkylmethyl, and benzyl; or, taken together, $R^2$ and $R^3$ are —$(CH_2)n$— where n is two to six, so as to form, with the nitrogen to which they are attached, a 3- to 7-membered heterocycle.

$R^4$ in Formula (I) is absent, or is selected from the group consisting of loweralkyl, loweralkenyl, loweralkynyl and benzyl; when present, $R^4$ is accompanied by a pharmaceutically acceptable counterion so as to form a quaternary ammonium salt.

$R^5$ in Formula (I) is selected from the group consisting of hydroxy and —$OR^9$, wherein $R^9$ is selected from lower alkyl, loweralkanoyl and —$S(O)_2CH_3$; or, taken together with $R^1$ and the carbons to which they are attached, $R^5$ forms a cyclic carbonate.

$R^6$ in Formula (I) is selected from the group consisting of hydrogen and loweralkyl.

$R^7$ in Formula (I) is selected from the group consisting of hydrogen and methyl.

In a further aspect of the present invention are provided pharmaceutical compositions for stimulating contractile motion of the gastrointestinal tract comprising a therapeutically effective amount of a compound of the invention and a pharmaceutically acceptable carrier.

In another aspect of the present invention is provided a method of treating disorders characterized by impaired gastrointestinal motility such as esophageal reflux, diabetic gastroparesis, pediatric gastroparesis, postoperative paralytic ileus, intestinal pseudoobstruction, gallbladder stasis, anorexia, gastritis, emesis and chronic constipation, comprising administering to a human or lower mammal in need of such treatment a therapeutically effective amount of a compound of the invention. In a related aspect, the present invention provides a method of facilitating the placement of diagnostic and therapeutic instrumentation, such as enteral feeding tubes, into the proximal small intestine comprising administering to a human or lower mammal in need of such treatment a therapeutically effective amount of an inventive compound.

In yet another aspect of the present invention is provided a process for the preparation of the above compounds, comprising one or more of the steps of (i) reacting a 4"-thiocarbonylimidazolyl derivative of an erythromycin with tris(trimethylsilyl)silane under conditions suitable for the formation of the corresponding 4"-deoxyerythromycin derivative; and (ii) reacting an 3'-N-desmethyl hemiketal derivative of an erythromycin with an alkyl halide, such as ethyl iodide, and a hindered base such as diisopropylethylamine, under conditions suitable for the formation of the corresponding 3'-N-desmethyl-3'-N-ethyl hemiketal erythromycin derivative.

DETAILED DESCRIPTION OF THE INVENTION

The present invention comprises novel compounds of Formula (I) and the pharmaceutically acceptable salts thereof which are gastrointestinal prokinetic agents. These compounds have been shown to be surprisingly potent motility enhancers, but to have only minimal antibacterial activity, in in vitro screening assays. Additionally, compounds of the invention have been tested in vivo, and have been found to possess an unexpected degree of bioavailability.

Preferred embodiments of the compounds of the invention are those of Formula (I) in which $R^{11}$ is methyl, and especially so those in which $R^1$ is hydrogen, i.e., those which are derivatives of erythromycin B. Also preferred are those compounds of Formula (I) in which $R^4$ is absent, and/or in which one of $R^2$ and $R^3$ is hydrogen or loweralkyl (other than methyl). Other substituents according to Formula (I) which result in the formation of preferred compounds of the invention are those in which (i) $R^5$ is hydroxy; (ii) $R^6$ is hydrogen; and/or (iii) $R^7$ is methyl.

Erythromycin derivatives which are representative of the compounds of the invention include the following:

8,9-anhydro-4"-deoxyerythromycin A-6,9-hemiketal;
8,9-anhydro-4"-deoxyerythromycin B-6,9-hemiketal;
8,9-anhydro-4"-deoxy-3'-N-desmethylerythromycin A-6, 9-hemiketal;
8,9-anhydro-4"-deoxy-3'-N-desmethyl-3'-N-ethylerythromycin A-6, 9-hemiketal;
8,9-anhydro-4"-deoxy-3'-N-propargylerythromycin A-6, 9-hemiketal bromide;
8,9-anhydro-4"-deoxy-3'-N-desmethylerythromycin B-6, 9-hemiketal;
8,9-anhydro-4"-deoxy-3'-N-desmethyl-3'-N-ethylerythromycin B-6, 9-hemiketal;
8,9-anhydro-4"-deoxy-3'-N-propargylerythromycin B-6, 9-hemiketal bromide;
9-deoxo-4",6-dideoxy-8-epi-6,9-epoxyerythromycin A;
9-deoxo-3'-N-desmethyl-4",6-dideoxy-8-epi-6,9-epoxyerythromycin A;
9-deoxo-3'-N-desmethyl-4",6-dideoxy-8-epi-3'-N-ethyl-6,9-epoxyerythromycin A;
9-deoxo-4",6-dideoxy-8-epi-6,9-epoxy-3'-N-propargylerythromycin A bromide;
9-deoxo-4",6-dideoxy-6,9-epoxyerythromycin A;
9-deoxo-3'-N-desmethyl-4",6-dideoxy-6,9-epoxyerythromycin A;
9-deoxo-3'-N-desmethyl-4",6-dideoxy-6,9-epoxy-3'-N-ethylerythromycin A; and
9-deoxo-4",6-dideoxy-6,9-epoxy-3'-N-propargylerythromycin A bromide.

Representative compounds of the present invention which are especially preferred are 8,9-anhydro-4"-deoxy-3'-N-desmethylerythromycin B-6,9-hemiketal and 8,9-anhydro-4"-deoxy-3'-N-desmethyl-3'-N-ethyl-erythromycin B-6, 9-hemiketal.

The term "amino-substituted loweralkyl" as used herein refers to a loweralkyl radical as defined below substituted with one or two amino groups.

The term "cyano-substituted loweralkyl" as used herein refers to a loweralkyl radical as defined below substituted with a cyano moiety.

The term "halo-substituted loweralkyl" as used herein refers to a loweralkyl radical as defined below substituted with one or two halogen atoms independently selected from fluorine, chlorine, bromine and iodine.

The term "hydroxy-substituted loweralkyl" as used herein refers to a loweralkyl radical as defined below substituted with one or two hydroxy groups.

The term "loweralkanoyl" as used herein refers to a radical having the formula —$C(O)R^{10}$ where $R^{10}$ is methyl or ethyl.

The term "loweralkenyl" as used herein refers to a $C_3$—to—$C_8$ straight or branched chain hydrocarbon radical having one double bond or, if $C_6$—to—$C_8$, optionally having a second double bond including, but not limited to, allyl, propenyl and the like.

The term "loweralkyl" as used herein refers to a $C_1$—to—$C_8$ straight or branched chain saturated hydrocarbon radical including, but not limited to, methyl, ethyl, n-propyl, isopropyl, n-butyl, sec-butyl, isobutyl, tert-butyl and the like.

The term "loweralkynyl" as used herein refers to a $C_3$—to—$C_8$ straight or branched chain hydrocarbon radical having one triple bond including, but not limited to, propynyl and the like.

The term "lowercycloalkyl" as used herein refers to a $C_3$—to—$C_7$ cyclic saturated hydrocarbon radical including, but not limited to, cyclopropyl, cyclobutyl and the like.

The term "lowercycloalkylmethyl" as used herein refers to a lowercycloalkyl radical radical as defined above connected via a methylene group including, but not limited to, cyclopropylmethyl, cyclobutylmethyl and the like.

The term "delayed gastric emptying" as used herein refers to a slow evacuation of gastric contents into the small intestine not caused by mechanical obstruction of the gastric outlet. Patients with severe gastric motor dysfunction may be incapacitated from intractable nausea, vomiting and gastric stasis. This may lead to failure to thrive in a young patient or to significant weight loss and malnutrition in adults. (Cf., "Medicine for the Practicing Physician Second Edition", J. Willis Hurst, ed., Butterworth Publishers, Boston (1988), pp. 1364–6.)

The term "gastroparesis" as used herein refers to paralysis of the stomach.

The term "intestinal pseudoobstruction" as used herein refers to a condition characterized by constipation, colicky pain and vomiting, but without evidence of organic obstruction apparent at laparotomy (abdominal surgery).

The term "paralytic or adynamic ileus" as used herein refers to obstruction of the intestines resulting from inhibition of bowel motility.

The term "reflux esophagitis" as used herein refers to inflammation of the esophagus as a result of frequent or chronic backward or return flow of stomach contents into the esophagus.

By "pharmaceutically acceptable salts" is meant those acid addition salts of the compounds of Formula (I) which are, within the scope of sound medical judgement, suitable for use in contact with the tissues of humans and lower animals without undue toxicity, irritation, allergic response, and the like commensurate with a reasonable benefit/risk ratio, and which are effective for their intended use.

Pharmaceutically acceptable salts are well known in the art. For example, S. M Berge, et al. describe pharmaceutically salts in detail in *J. Pharmaceutical Sciences* (1977), 66: 1–19. Examples of pharmaceutically acceptable, non-toxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the are such as ion exchange. Other pharmaceutically acceptable salts include nitrate, bisulfate, borate, formate, butyrate, valerate, 3-phenylpropionate, camphorate, adipate, benzoate, oleate, palmitate, stearate, laurate, lactate, fumarate, ascorbate, aspartate, nicotinate, p-toluenesulfonate, camphorsulfonate, methanesulfonate, 2-hydroxyethanesulfonate, gluconate, glucoheptonate, lactobionate, glycerophosphate, pectinate, lauryl sulfate, alginate, cyclopentanepropionate, digluconate, dodecylsulfate, ethanesulfonate, hemisulfate, heptonate, hexanoate, 2-naphthalenesulfonate, pamoate, persulfate, pivalate, propionate, undecanoate salts and the like, and may be prepared according to conventional methods. Representative alkali or alkaline earth metal salts include sodium, calcium, potassium, magnesium salts and the like. Pharmaceutically acceptable counterions for the quaternary ammonium salt compounds formed when $R^4$ is present include halide (especially bromide and iodide), hydroxide, carboxylate, sulfate, phosphate, nitrate, loweralkyl sulfonate and arysulfonate.

As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible substances used in pharmaceutical formulations. Wetting agents, emulsifiers and lubricants such as sodium lauryl sulfate and magnesium stearate, as well as coloring agents, releasing agents, coating agents, sweetening, flavoring and perfuming agents, preservatives and antioxidants can also be present in the composition, according to the judgement of the formulator.

By a "therapeutically effective amount" of a compound of the invention is meant a sufficient amount of the compound to treat a gastrointestinal disorder, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts, for example, of from about 0.0001 to about 25 mg/kg body weight. More preferably, daily doses may range from about 0.0005 to about 10 mg/kg or, even more preferably, from about 0.005 to about 2 mg/kg body weight. Single dose compositions may contain such amounts or submultiples thereof as make up the daily dose. In general, treatment regimens according to the present invention comprise administration to a human patient in need of such treatment of from about 1 mg to about 100 mg of the compound(s) of this invention per day in multiple doses or in a single dose.

Liquid dosage forms for oral administration may include pharmaceutically acceptable emulsions, microemulsions, solutions, suspensions, syrups and elixirs containing inert diluents commonly used in the art such as water. Such compositions may also comprise adjuvants such as wetting agents; emulsifying or suspending agents and sweetening, flavoring or perfuming agents.

Injectable preparations, as for example sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, as for example in solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid may be used in the preparation of injectables.

The injectable formulation can be sterilized, as for example by filtration through a bacteria-retaining filter or by incorporating sterilizing agents in the form of sterile solid compositions which can be dissolved or dispersed in sterile water or other sterile injectable medium just prior to use.

In order to prolong the effect of a drug, it is often desirable to slow the absorption of a drug from subcutaneous or intramuscular injection. The most common way to accomplish this is to inject a suspension of crystalline or amorphous material with poor water solubility. The rate of absorption of the drug becomes dependent on the rate of dissolution of the drug which is, in turn, dependent on the physical state of the drug, as for example, its crystal size and crystalline form. Another approach to delaying absorption of a drug is to administer the drug as a solution or suspension in oil. Injectable depot forms can also be made by forming microcapsule matrices of drugs and biodegradable polymers such as polylactide-polyglycolide. Depending on the ratio of drug to polymer and the composition of the polymer, the rate of drug release can be controlled. Examples of other biodegradable polymers include poly-orthoesters and polyanhydrides. The depot injectables can also be made by entrapping the drug in liposomes or microemulsions which are compatible with body tissues.

Solid dosage forms for oral administration may include capsules, tablets, pills, powders, prills and granules. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such as magnesium stearate and microcrystalline cellulose. In the case of capsules, tablets and pills, the dosage forms may also comprise buffering agents. Tablets and pills can additionally be prepared with enteric coatings and other release-controlling coatings.

Solid compositions of a similar type may also be employed as fillers in soft and hard-filled gelatin capsules using such exipients as lactose or milk sugar as well as high molecular weight polyethylene glycols and the like.

The active compounds can also be combined in microencapsulated form with one or more excipients as noted above. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferably, in a certain part of the intestinal tract, optionally in a delayed manner. Examples of embedding compositions which can be used include polymeric substances and waxes.

Further improvements in the delivery of the compounds of the invention may be accomplished by the fcrmation of biolabile derivatives, or prodrugs, which upon administration to a patient are converted in vivo to the parent compound. Prodrugs are well-known in the art, and may be prepared by the addition, as for example by esterification or other derivatization at the 2'position of the present compounds, of a pharmaceutically acceptable and biologically cleavable group. (A thorough discussion of prodrugs is provided in T. Higuchi and V. Stella, "Pro-drugs as Novel Delivery Systems", Vol 14 of the A.C.S. Symposium Series, and in *Bioreversible Carriers in Drug Design*, ed. Edward B. Roche, American Pharmaceutical Association and Pergamon Press, 1987, both of which are incorporated herein by reference.) It is expected that such prodrugs will be readily apparent to the skilled reader and will be regarded as functional equivalents of the compounds of the invention.

The compounds of the present invention may be synthesized by the reaction Schemes I through VI presented below, in which $R^1$–$R^3$ correspond to the groups defined with respect to Formula (I).

Scheme I

Erythromycin A or B is treated with a suitable reagent for acetylating the 2'-hydroxyl group, such as acetic anhydride or acetyl chloride. The 2'-O-acetyl compound of formula 2 is converted to a compound of formula 3 by treatment with 1,1'-thiocarbonyldiimidazole in a suitable solvent, such as methylene chloride, benzene, toluene and the like, at room temperature to give the 4"-thiocarbonylimidazolyl derivative 3. Subsequently, the 4"-thiocarbonylimidazolyl group is eliminated by reaction of 3 with tributyltin hydride and $\alpha,\alpha$-azobis(isobutyronitrile) (AIBN) in an inert-reaction solvent such as toluene, benzene, and the like at 110° C. for 4 to 5 hours to give the 4"-deoxy compound 4. The compound of formula 4 is subjected to solvolysis at the 2'-O-acetylated position to give a compound of formula 5 which is converted to the hemiketal of formula 6 with an appropriate nonaqueous acid, such as glacial acetic acid.

In a preferred and novel modification of the above synthesis, the above elimination reaction of 3 with tributyltin hydride is instead carried out with tris(trimethylsilyl) silane, $(Me_3Si)_3SiH$. This improvement provides a 4"-deoxy intermediate 4 which is more readily purified in the subsequent reaction steps.

Scheme 2

The dimethylamino group in the desosamine moiety of the hemiketal of formula 6, prepared as described in Scheme 1, above may be modified to the 3'-N-desmethyl hemiketal derivative by treatment with iodine in the presence of a suitable base, such as sodium acetate, followed by the addition of sodium thiosulfate to yield the compound of formula 7. Hydrogenation of 7 in the presence of acetaldehyde gives the 3'-N-desmethyl-3'-N-ethyl hemiketal derivative 8. Reaction of 8 with a suitable alkylating agent, such as propargyl bromide in acetonitrile gives the 3'-N-propargyl erythromycin hemiketal derivative 9.

Other alkylating agents which may be used in preparing compounds of Formula 9 include loweralkyl halides such as ethyl bromide, halo-substituted loweralkyl halides, cyano-substituted loweralkyl halides, hydroxy-substituted loweralkyl halides, other loweralkenyl halides such as methylallyl chloride, loweralkynyl halides such as propargyl bromide, lower cycloalkyl halides, lower cycloalkylmethyl halides such as lower cyclopropylmethyl and benzyl halides.

As a preferred alternative to the above hydrogenation/alkylation step (involving an acetaldehyde), the intermediate 7 may be reacted with an alkyl halide, as for example ethyl iodide, and a hindered base, as for example diisopropylethylamine, to form the 3'-N-desmethyl-3'-N-ethyl hemiketal derivative 8. This novel reaction goes more readily to completion, and accordingly produces better yields, than the previously described hydrogenation.
Scheme 1
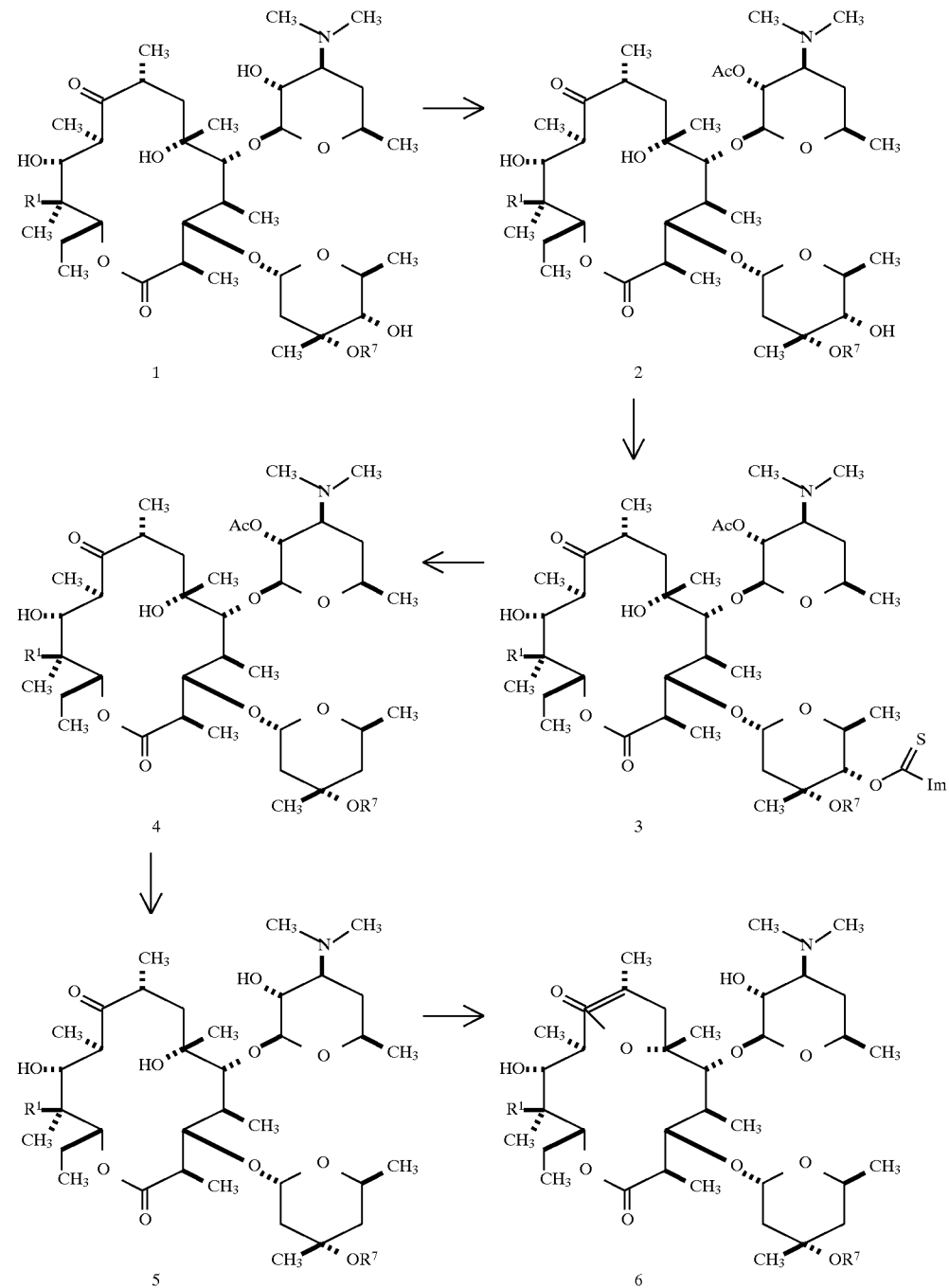

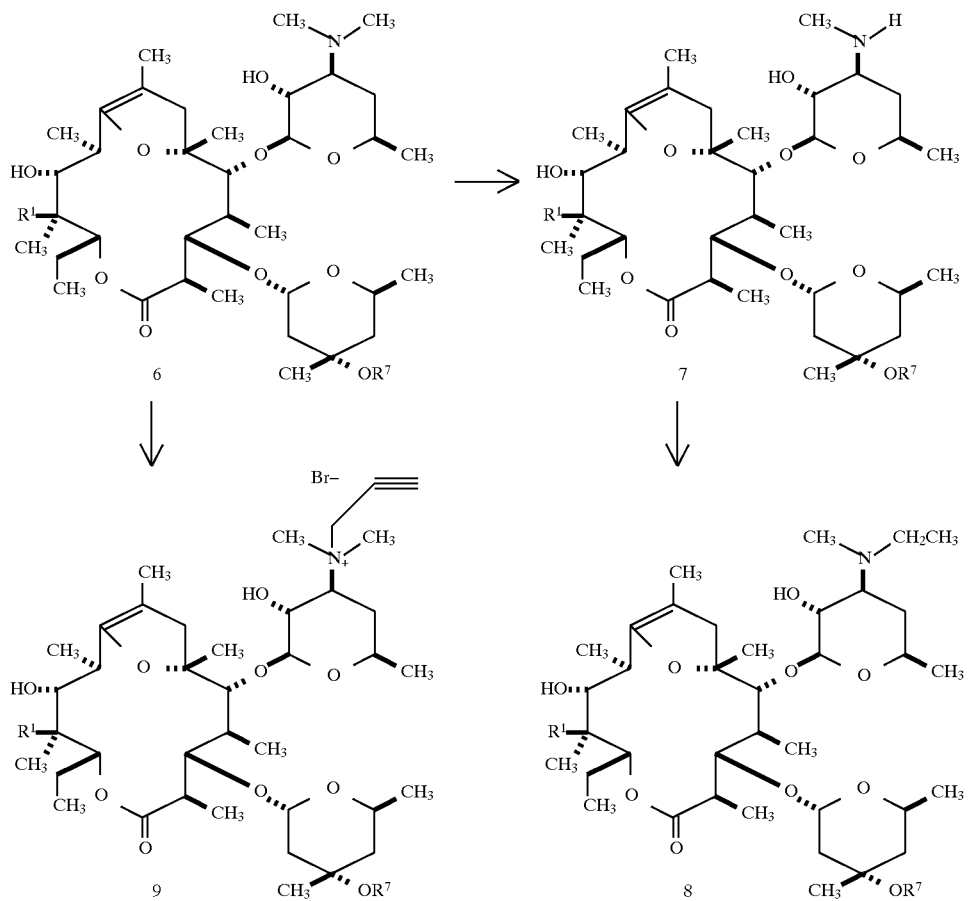

Scheme 2

Scheme 3

The 8,9-anhydro-4"-deoxyerythromycin hemiketal derivative of formula 6 may also be converted to the epoxyerythromycin derivative of formula 10 by hydrogenation in the presence of a suitable catalyst such as platinum.

Modifications of the 3'-N-dimethylamino group in the desosamine moiety of the epoxyerythromycin derivative is as described in Scheme 2, and yields the N-desmethyl-, N-desmethyl-N-ethyl-, and N-propargyl-epoxyerythromycin derivatives (respectively 11, 12 and 13).

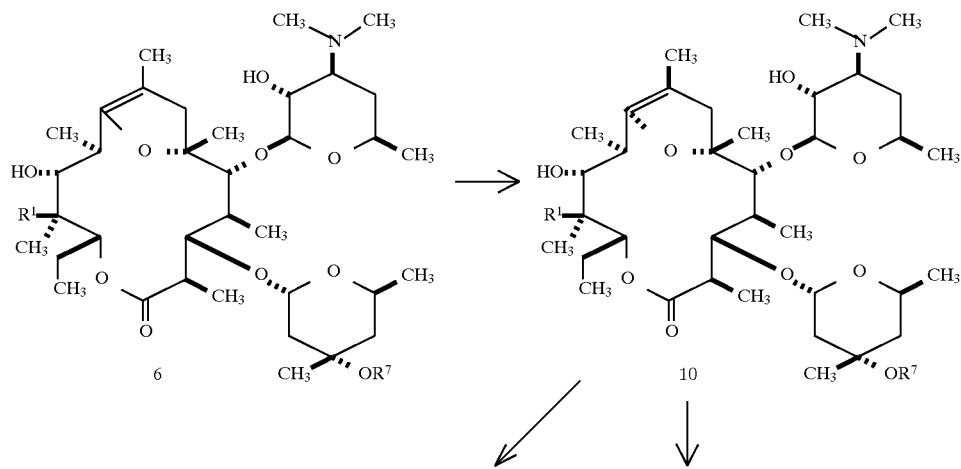

Scheme 3

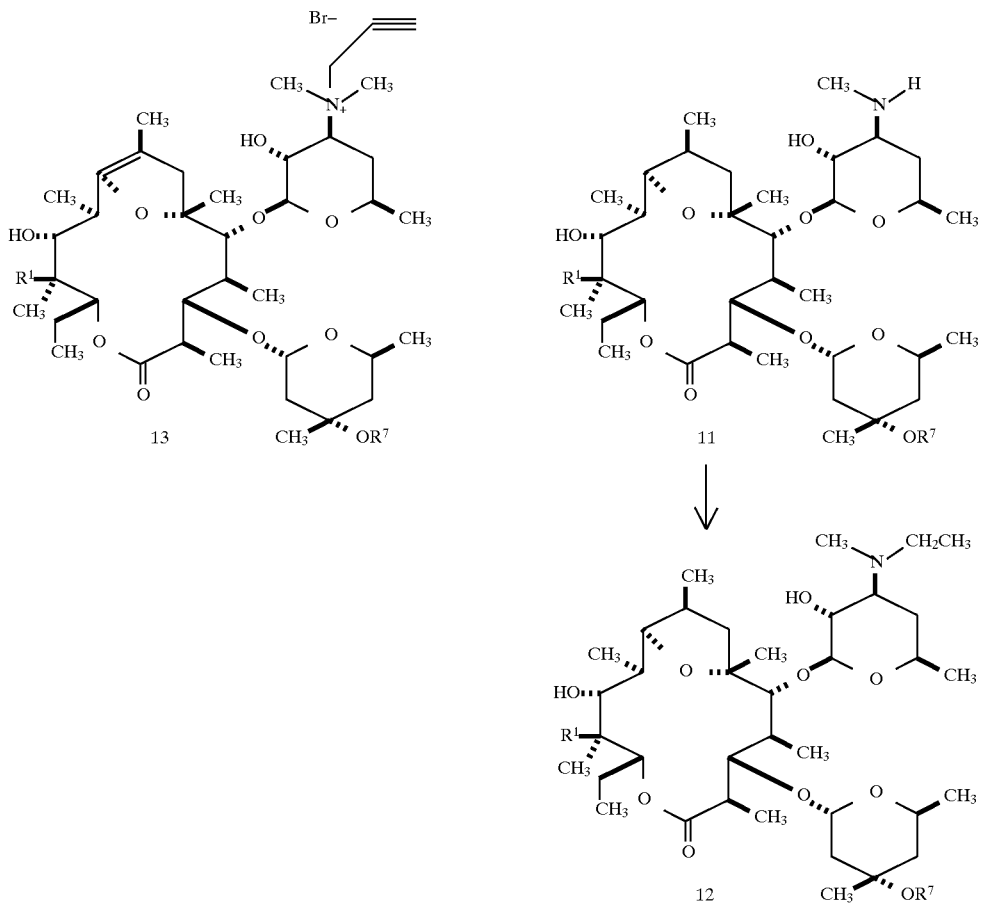

Scheme 4

The 2'-O-acetyl-4"-deoxyerythromycin, Formula 4, prepared as described in Scheme 1, above, may be converted to the 11,12-carbonate by treatment with a suitable carbonic acid derivative such as ethylene carbonate, carbonyldiimidazole, or thiocarbonyl diimidazole to afford a carbonate derivative of Formula 14. In the presence of a suitable solvent, such as isopropanol, 14 is reacted with sodium borohydride at room temperature for several hours to yield 15. The compound of formula 15 is converted to the epoxy derivative 16 by reaction with trifluoromethanesulfonic anhydride in the presence of a suitable solvent, such as pyridine. Intermediate 16 may be deacetylated in the presence of an alcoholic solvent (e.g., ethanol, methanol or the like) at room temperature for several hours to obtain compound 17. 17 in turn may be treated with a suitable base, such as postassium carbonate, to afford the compound of formula 18.

Scheme 5

Modifications of the 3'-N-dimethylamino group in the desosamine moiety of the epoxyerythromycin derivative of Formula 18 (prepared as described above in Scheme 4) are as described in Scheme 2 to yield the N-desmethyl, N-desmethyl-N-ethyl-, and N-propargyl-epoxyerythromycin derivatives (respectively 19, 20 and 21).

Scheme 6

Compounds of Formula (I) in which $R^1$ is methyl and $R^{11}$ is hydrogen (i.e., derivatives of 12-epierythromycin B) may be prepared beginning with the following rearrangement at the C-12 position. The compound of formula 2 is converted to compound 22 by treatment with benzyloxycarbonyl chloride for 24 hours at about 20° C., in a suitable solvent such as methylene chloride, using a suitable base such as 4-N, N-dimethylaminopyridine. Intermediate 22 is subsequently treated with thiophosgene in a solvent such as tetrahydrofuran, in the presence of a base such as sodium hexamethyldisilazide, at about −78° C. for 1 to 2 hours to provide the thiocarbonate compound 23.

Compound 23 is next treated with tributyltin hydride and α,α-AIBN in a solvent such as toluene to provide the compound of formula 24, from which the 2'-O-acetyl group is removed as by refluxing in methanol and subsequent chromatographic purification. The resulting compound of formula 25 is then 15  16
Scheme 4
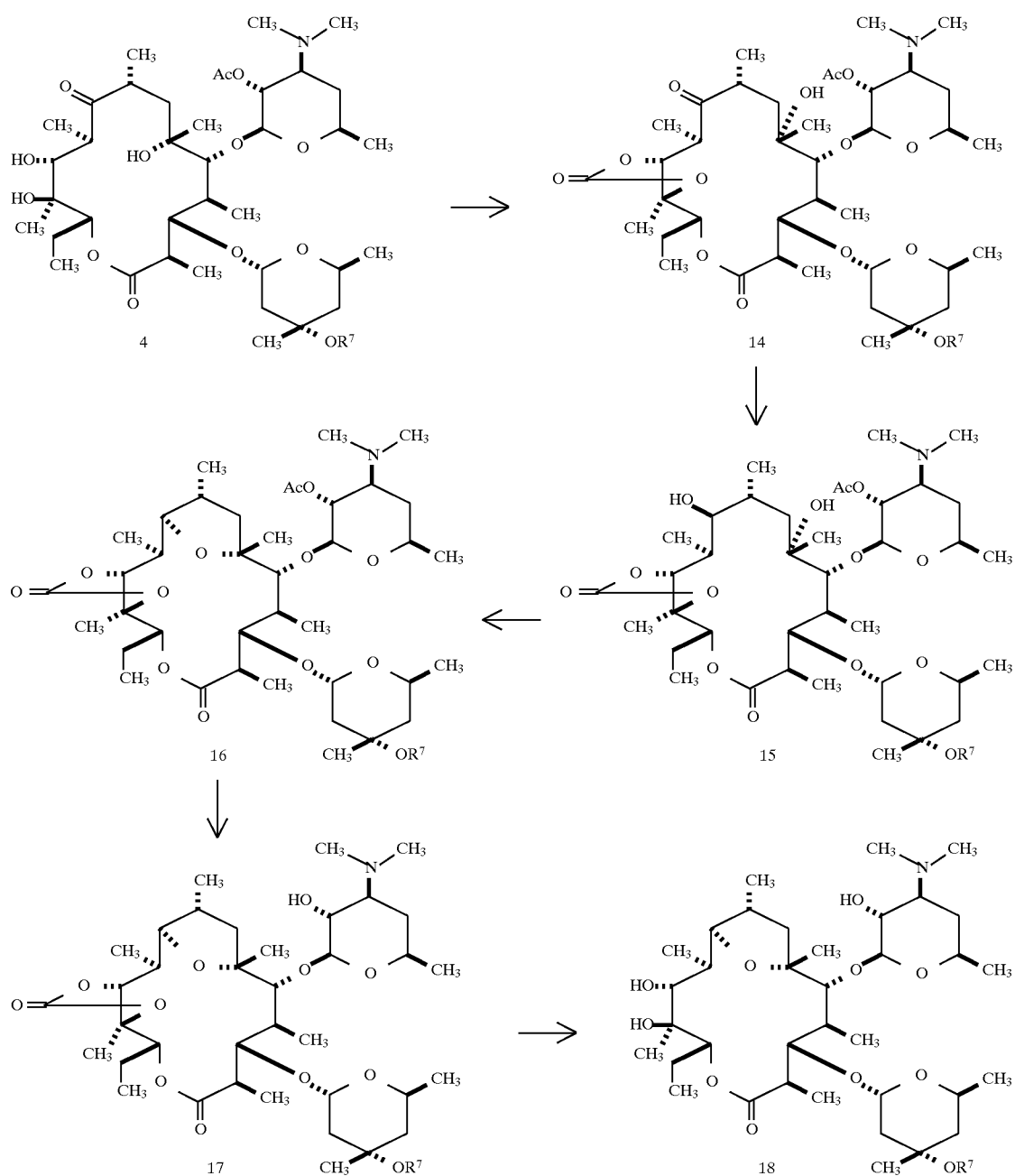

Scheme 5
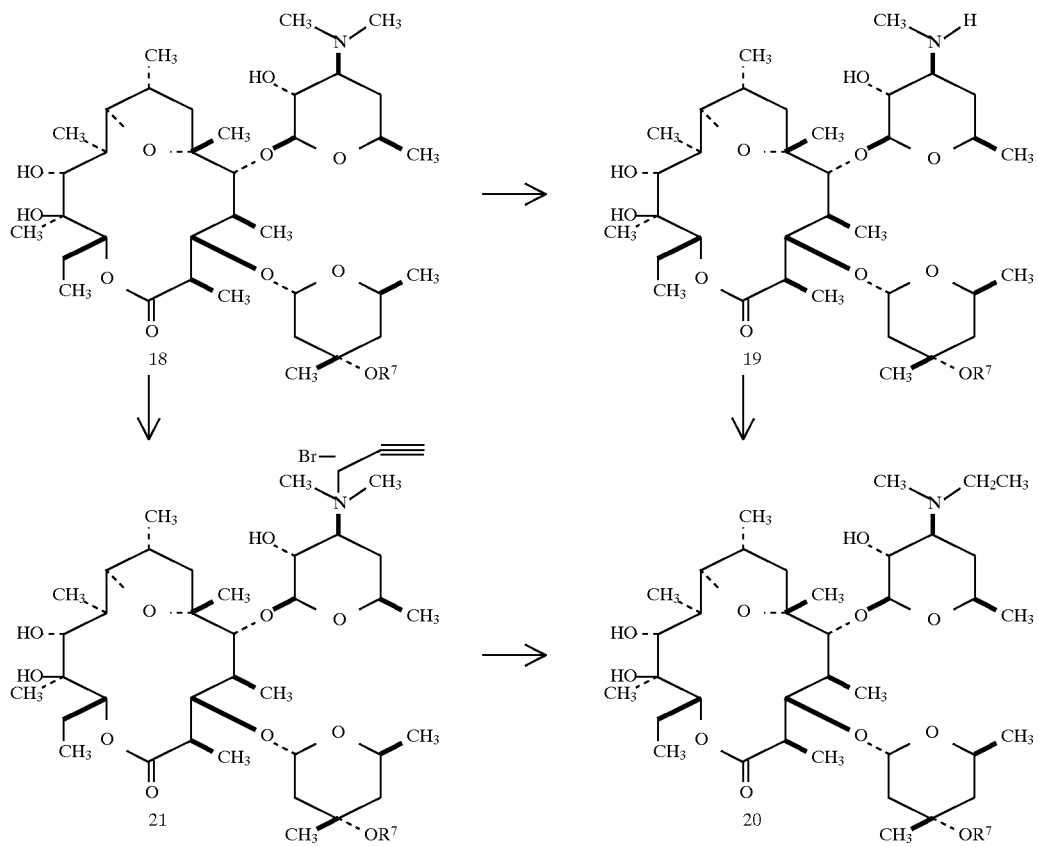
dissolved in a solvent such as methanol and the carbobenzyloxycarbonyl group removed by hydrogenolysis at room temperature and over 10% Pd/C for about 1 hour to provide the hemiketal of formula 26. Subsequent elimination of the 4"-hydroxy group, using the chemistry disclosed elsewhere herein, results in the 12-epi compounds of the present invention.
Scheme 6
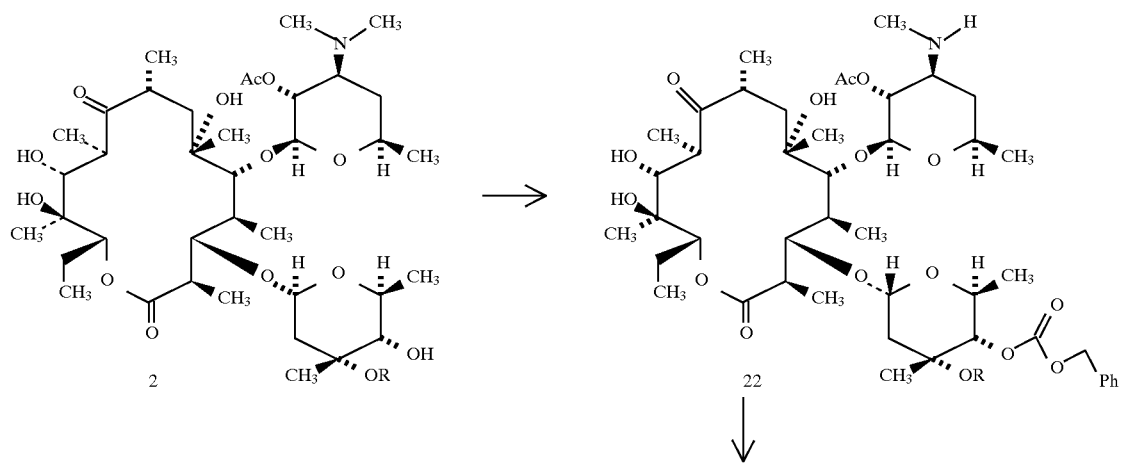

-continued
Scheme 6

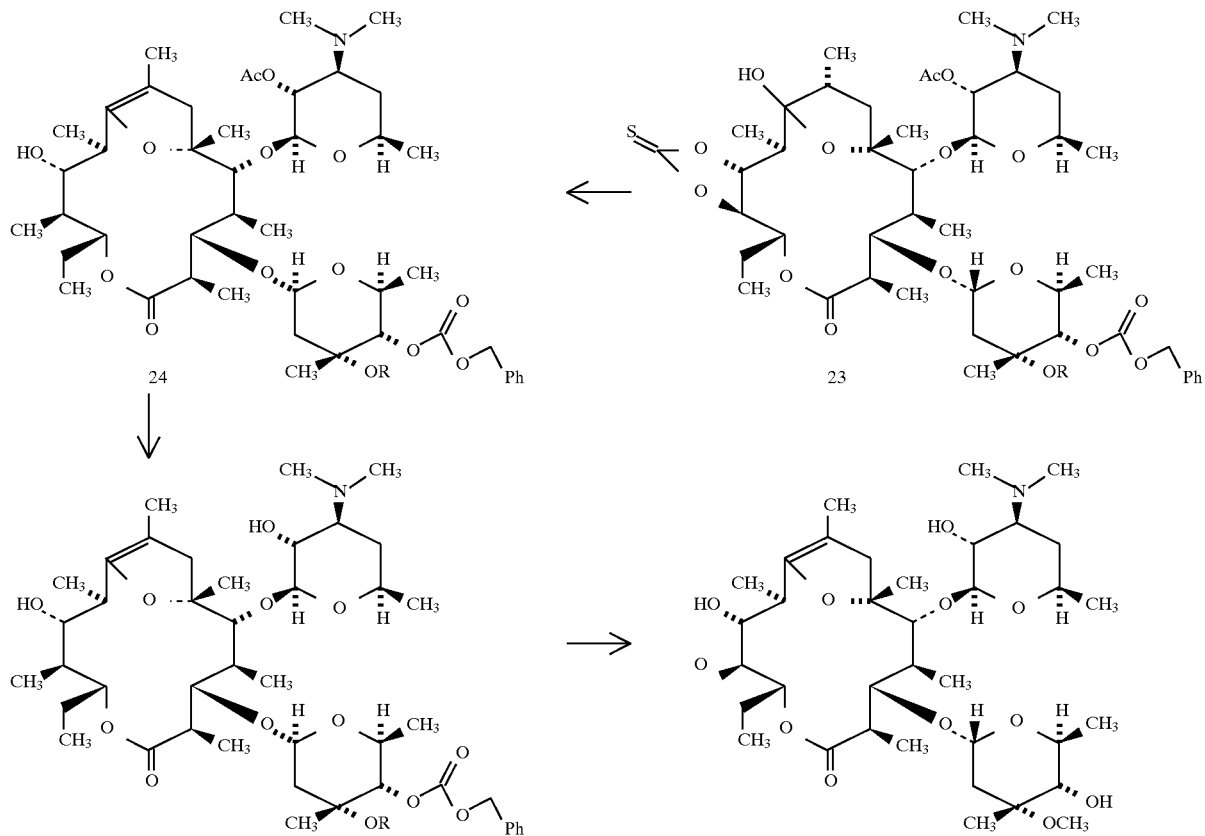

The foregoing schemata may be better understood by reference to the following examples, which are provided for illustration only and are not intended as a limitation of the invention.

EXAMPLE 1

8,9-Anhydro-4"-deoxyerythromycin A-6,9-hemiketal

Step 1: 2'-O-Acetylerythromycin A (1-1)

Acetic anhydride (3.5 ml, 1.2 eq.) was added at ambient temperature to a solution of erythromycin A (23 g, commercially available from Abbott Laboratories) dissolved in 350 mL of methylene chloride. The reaction mixture was stirred for 12 hours at room temperature. The methylene chloride solution was washed twice with 100 mL of 1% sodium bicarbonate solution, once with 100 mL of water, dried over anhydrous sodium sulfate and filtered. Solvent was removed in vacuo to afford a white solid which was recrystallized from acetonitrile to the product in 71% yield.

Step 2: 2'-O-acetyl-4"-O-imidazolyl thionocarbonylerythromycin A (1-2)

To a solution of 2'-O-acetylerythromycin A (9.75 g, 12.565 mmol, prepared as described in Step 1, above) in 100 mL of methylene chloride was added dimethylaminopyridine (3.07 g, 0.0253 mol), followed by 1,1'-thiocarbonyldiimidazole (3.36 g, 18.85 mmol) with stirring at room temperature for 16 hours at which time an additional 0.5 eq of 1,1'-thiocarbonyldiimidazole was added, The reaction continued for another 12 hours. The mixture was diluted with 100 mL of methylene chloride and washed consecutively with 150 mL of sodium bicarbonate, water (three timesx100 mL), and with 200 mL of brine. The resulting solution was filtered and dried over sodium sulfate in vacuo to yield 2'-O-acetyl-4"-O-imidazolylthionocarbonylerythromycin A.

Step 3: 2'-O-Acetyl-4"-Deoxyerythromycin A (1-3)

Nitrogen gas was bubbled through a solution of 2'-O-acetyl-4"-O-imidazolylthionocarbonylerythromycin A (1.0 g, 1.1 mmol, prepared as in Step 2, above) in 50 mL of dry toluene while heating at 110° C. To this solution was added tributyltin hydride (0.4 mL, 1.2 eq), α,α-AIBN (18 mg), and 5 mL of toluene over a period of 5 h at 110° C. At the end of the addition, the mixture was stirred for an additional 30 min. The solvent was evaporated and the crude product purified over silica gel (CHCl₃:CH₃OH:NH₄OH; 95:5:0.5) to give the title compound in 65% yield.

Step 4: 4"-Deoxyerythromycin A

2'-O-Acetyl-4"-Deoxyerythromycin A (1.48 g, 2.0 mmol, prepared as described in Step 3, above) was dissolved in 50 mL of methanol and heated to reflux for 4 hours and stirred at room temperature overnight. Solvent was removed in vacuo and the crude product chromatographed over silica gel (CHCl₃:CH₃OH:NH₄OH; 95:5:0.5) to yield the title compound in 70% yield.

Step 5: 8,9-anhydro-4"-deoxyerythromycin A-6,9-hemiketal

4"-Deoxyerythromycin A (160 mg, 2.0 mmoL, prepared as described in Step 4, above) was dissolved in glacial acetic acid and stirred at room temperature for 3 hours. The acetic acid was evaporated in vacuo from the mixture at 40° C. The crude product was dissolved in 50 mL of methylene chloride and washed consecutively with 30 mL of cold saturated sodium bicarbonate, 30 mL of water, and 30 mL of brine.

The solution was dried over sodium sulfate and chromatographed over silica gel (CHCl$_3$:CH$_3$OH:NH$_4$OH; 100:10:1) to yield the title compound in 59% yield.

EXAMPLE 2

8,9-anhydro-4"-deoxyerythromycin B-6,9-hemiketal
Step 1: 2'-O-Acetylerythromycin B (2-1)

The title compound (44 g, 62.9 mmol, 86% yield) was prepared by the procedure of Example 1, Step 1, except erythromycin B was used instead of erythromycin A.

Step 2: 2'-O-acetyl-4"-O-imidazolylthionocarbonylerythromycin B (2-2)

The title compound (57% yield) was prepared by the procedure of Example 1, Step 2, except 2'-O-acetylerythromycin B (2.97 g, 4.0 mmol) was used instead of 2'-O-acetylerythromycin A.

Step 3: 2'-O-Acetyl-4"-Deoxyerythromycin B (2-3)

The title compound (44% yield) was prepared by the procedure of Example 1, Step 3, except 2'-O-acetyl-4"-O-imidazolylthionocarbonylerythromycin B (1.93 g, 0.0022 moL) was used instead of 2'-O-acetyl-4"-O-imidazolylthionocarbonylerythromycin A.

Step 4: 4"-Deoxyerythromycin B (2-4)

The title compound (73% yield) was prepared by the procedure of Example 1, Step 4, except 2'-O-acetyl-4"-deoxyerythromycin B (100 mg, 1.0 mmoL) was used instead of 2'-O-acetyl-4"-deoxyerythromycin A.

Step 5: 8,9-anhydro-4"-deoxyerythromycin B-6,9-hemiketal

The title compound (85% yield) was prepared by the procedure of Example 1, Step 5, except 4"-deoxyerythromycin B (60 mg, 0.08 mmoL) was used instead of 4"-deoxyerythromycin A.

EXAMPLE 3

8,9-anhydro-4"-deoxy-3'-N-desmethyl erythromycin A-6,9-hemiketal 8,9-anhydro-4"-deoxyerythromycin A-6,9-hemiketal (170 mg, 0.24 mmol, prepared as described in Example 1, above) was dissolved in 10 mL of methanol. Sodium acetate (189 mg, 5.73 eq.) and iodine (70 mg, 1.13 eq.) were added and the mixture stirred with exposure to light for 2 hours. Ten percent sodium thiosulfate was added dropwise with stirring to decolorize the mixture. Methylene chloride (100 mL) was added and the mixture washed with 20 mL of 10% sodium bicarbonate, 20 mL water, followed by filtration and evaporation of the filtrate in vacuo. The crude product was chromatographed over silica gel (CHCl$_3$:CH$_3$OH:NH$_4$OH; 90:10:1.0) to yield the title compound in 91% yield.

EXAMPLE 4

8,9-anhydro-4"-deoxy-3'-N-desmethyl-3'-N-ethylerythromycin A-6,9-hemiketal 8,9-anhydro-4"-deoxy-3'-N-desmethylerythromycin A-6,9-hemiketal (69 mg, 0.1 mmoL, prepared as described in Example 3, above) was dissolved in 20 mL methanol and hydrogenated at 4 atmospheres for 12 hours in the presence of 0.1 mL of acetaldehyde and over 100 mg of 10% Pd/C. The mixture was filtered and solvent removed in vacuo. The crude product was chromatographed over silica gel (CHCl$_3$:CH$_3$OH:NH$_4$OH; 95:5:0.5) to yield the title compound (65%).

EXAMPLE 5

8,9-anhydro-4"-deoxy-3'-N-propargylerythromycin A-6,9-hemiketal bromide

To a solution of 8,9-anhydro-4"-deoxyerythromycin A-6,9-Hemiketal (25 mg, 0.035 mmol, prepared as described in Example 4, above) in acetonitrile was added propargyl bromide (80% by weight in toluene, 3.1 eq, 0.010 mL) and the mixture stirred for 5 hours. The solvent was evaporated and the mixture triturated with several 10 mL portions of ethyl acetate. The title compound was obtained as a white residue which was dried in vacuo to yield the title compound (92%).

EXAMPLE 6

8,9-anhydro-4"-deoxy-3'-N-desmethylerythromycin B-6,9-hemiketal 8,9-anhydro-4"-deoxyeryt hromycin B-6,9-hemiketal (112 mg, 0.17 mmol, prepared as described in Example 2, above) was reacted as described in Example 3, above, to yield the title compound as a white solid (83% yield).

EXAMPLE 7

8,9-anhydro-4"-deoxy-3'-N-desmethyl-3'-N-ethyleryhromycin B-6,9-hemiketal 8,9-anhydro-4"-deoxy-3'-N-desmethylerythromycin B-6,9-hemiketal (62 mg, 0.01 mmol, prepared as described in Example 6, above) was reacted as described in Example 4, above, to yield the title compound (65%).

EXAMPLE 8

8,9-anhydro-4"-deoxy-3'-N-propargylerythromycin B-6,9-hemiketal bromide 8,9-anhydro-4"-deoxyerythromycin B-6,9-hemiketal (22 mg, 0.03 mmol) prepared as described in Example 2, above) was dissolved in 3 mL of dry acetonitrile. Propargyl bromide (3.1 eq.) was added and the mixture subjected to the conditions of Example 5, above to yield the title compound (92%).

EXAMPLE 9

9-deoxo-4",6-dideoxy-8-epi-6,9-epoxyerythromycin A

A solution of 8,9-anhydro-4"-deoxyerythromycin A-6,9-hemiketal (212 mg, 0.03 mmol, prepared as described in Example 1, above) in 20 mL glacial acetic acid containing difluoroacetic acid (2.0 eq.) was hydrogenated over platinic oxide (200 mg) for 12 hours. Ammonium acetate (100 mg) was added and stirred for 30 min. The mixture was filtered and the solvents removed in vacuo at 40° C. The residue was re-suspended in 50 mL chloroform, washed twice with 25 mL sodium bicarbonate and once with 25 mL water. The organic phase was dried over sodium sulfate, filtered and the solvent removed in vacuo to afford a residue which was purified by chromatography over silica gel (CHCl$_3$:CH$_3$OH:NH$_4$OH; 95:5:0.5) to give the title compound in 42% yield.

EXAMPLE 10

9-deoxo-3'-N-desmethyl-4",6-dideoxy-8-epi-6,9-epoxyerythromycin A 9-deoxo-4",6-dideoxy-8-epi-6,9-epoxyerythromycin A (171 mg, 0.24 mmoL, prepared as described in Example 9, above) was reacted as described in Example 3, above to give the title compound in 63% yield.

EXAMPLE 11

9-deoxo-3'-N-desmethyl-4",6-dideoxy-8-epi-3'-N-ethyl-6,9-epoxyerythromycin A 9-deoxo-3'-N-desmethyl-4",6-dideoxy-8-epi-6,9-epoxyerythromycin A (90 mg, 0.13 mmoL, prepared as described in Example 10, above) was reacted as described in Example 4, above to yield the title compound in 53% yield.

EXAMPLE 12

9-deoxo-4",6-dideoxy-8-epi-6,9-epoxy-3'-N-proparqylerythromycin A bromide 9-deoxo-4",6-dideoxy-8-epi-6,9-epoxyerythromycin A (21.5 mg, 0.031 mmoL, prepared as described in Example 9, above) in acetonitrile was added propargyl bromide (80% by weight in toluene, 3.1 eq, 0.010 mL) at room temperature and stirred for 6 hours. The solvent was evaporated and the resulting residue triturated with ethyl acetate as described in Example 5, above to give the title compound in 93% yield.

EXAMPLE 13

9-deoxo-4",6-dideoxy-6,9-epoxyerythromycin A

Step 1: 2'-O-Acetyl-11,12-O-Carbonyl-4"-Erythromycin A (13-1)

2'-O-Acetyl-4"-deoxyerythromycin A (340 mg, 0.45 mmoL, prepared as described in Example 1, step 3, above) was dissolved in 5 mL toluene. Carbonyldiimidazole (290 mg, 1.79 mmol) and dimethylaminopyridine (112 mg, 0.9 mmol) were added and the mixture stirred at 80° C. for 2.5 hours. Methylene chloride (100 mL) was added and the mixture washed sequentially with 50 mL brine and 50 mL water. The organic phase was dried over sodium sulfate, filtered and evaporated to yield a residue which was purified on silica gel chromatography ($CH_3CN:NH_4OH$; 100:2) to afford 2'-O-acetyl-11,12-O-carbonyl-4"-erythromycin A (yield 73%).

Step 2: 2'-O-Acetyl-11,12-O-Carbonyl-4"-Deoxy-9,9-Dihydroerythromycin. A (13-2)

2'-O-acetyl-11,12-O-carbonyl-4"-deoxyerythromycin A (250 mg, 0.32 mmol, prepared as described in Step 1, above) was dissolved in 5 mL isopropanol. Sodium borohydride (72 mg, 1.9 mmol) was added and the mixture stirred at room temperature for 8 h and then left to stand at 0° C. for an additional 12 hours. Phosphate buffer was added to adjust the pH of the mixture to 7, followed by addition of 50 mL of methylene chloride. The mixture was extracted three times with 50 mL of phosphate buffer and once with 50 mL of water. The resulting organic phase was dried over sodium sulfate, filtered, and evaporated in vacuo to give a residue which was purified over silica gel chromatography ($CH_3CN:NH_4OH$; 98:2) to give 2'-O-acetyl-11,12-O-carbonyl-4"-deoxy-9,9-dihydroerythromycin A.

Step 3: 2'-O-Acetyl-11,12-O-Carbonyl-9-deoxo-4",6-Dideoxy-6,9-epoxyerythromycin A (13-3)

2'-O-acetyl-11,12-O-carbonyl-4"-deoxy-9,9-dihydroerythromycin A.(100 mg, 0.126 mmol, prepared as described in Step 2, above) was dissolved in methylene chloride and the solution cooled to −10° C. Pyridine (0.05 mL) and trifluoromethanesulfonic anhydride (0.05 mL, 0.63 mmoL) were added and the mixture stirred at −10° C. for 3 hours. Saturated aqueous sodium bicarbonate (10 mL) was added, followed by 10 mL methylene chloride. The mixture was shaken and the organic phase subsequently washed with 10 mL of brine and 10 mL of water, dried over sodium sulfate, filtered and the filtrate evaporated in vacuo. The residue was purified over silica gel ($CHCl_3:MeOH:NH_4OH$; 95:5:0.5) to afford 2'-O-acetyl-11, 12-O-carbonyl-9-deoxo-4',6-dideoxy-6,9-epoxyerythromycin A (75% yield).

Step 4: 11,12-O-Carbonyl-9-deoxo-4",6-Dideoxy-6,9-epoxyerythromycin A (13-4)

2'-O-acetyl-11,12-O-carbonyl-9-deoxo-4',6-dideoxy-6,9-epoxyerythromycin A (70 mg, 0.09 mmol, prepared as described in Step 3, above) was dissolved in methanol and the mixture stirred at room temperature for 12 hours. The solvent was removed in vacuo and the residue purified by silica gel chromatography ($CHCl_3:MeOH:NH_4OH$; 95:5:0.5) to afford 11,12-O-carbonyl-9-deoxo-4',6-dideoxy-6,9-epoxyerythromycin A (94% yield).

Step 5: 9-deoxo-4",6-dideoxy-6,9-epoxyerythromycin A 11,12-O-carbonyl-9-deoxo-4',6-dideoxy-6,9-epoxyerythromycin A (51 mg, 0.07 mmol, prepared as described in Step 4, above) was dissolved in 3 mL of methanol. Potassium carbonate (13.5 mg, 0.09 mmol) was added and the mixture stirred at room temperature for two days. Methylene chloride (25 mL) was added and the mixture partitioned twice with 15 mL of phosphate buffer and sequentially with 25 mL of brine and 20 mL of water. The organic phase was dried over sodium sulfate, filtered and evaporated in vacuo. The residue was chromatographed over silica gel ($EtOAc:MeOH:NH_4OH$; 10:0.5:0.5) to afford 9-deoxo-4',6-dideoxy-6,9-epoxyerythromycin A (45% yield).

EXAMPLE 14

9-Deoxo-4',6-Dideoxy-3'-N-Desmethyl-6.9-Epoxyerythromycin A 9-deoxo-4",6-dideoxy-6,9-epoxyerythromycin A (151 mg, 0.21 mmol, prepared as described in Example 13, above) was dissolved in 10 ml of methanol and reacted as described in Example 3, above to yield the title compound which was purified by silica gel chromatography ($EtOAc:MeOH:NH_4OH$; 10:0.5:0.3) to 91% yield.

EXAMPLE 15

9-deoxo-3'-N-desmethyl-4",6-dideoxy-6,9-epoxy-3'-N-ethylerythromycin A 9-deoxo-3'-N-desmethyl-4",6-dideoxy-6,9-epoxyerythromycin A (91 mg, 0.013 mmol, prepared as described in Example 14, above) was reacted as described in Example 4 to yield the title compound (74% yield).

EXAMPLE 16

9-deoxo-4",6-dideoxy-6,9-epoxy-3'-N-propargylerythromycin A bromide

9-Deoxo-4",6-dideoxy-6,9-epoxyerythromycin A (26 mg, 0.037 mmol, prepared as described in Example 13, above) was reacted as described in Example 3, above to yield the title compound (100% yield).

EXAMPLE 17

8,9-anhydro-12-epierythromycin B-6,9-hemiketal

Step 1: 2"-O-acetyl-11-O-benzyloxycarbonylerythromycin A (17-1)

2"-O-acetylerythromycin A (9.75 g, 13 mmol) (prepared as in Example 1, Step 1) was dissolved in 60 mL of methylene chloride. Dimethyl Aminopyridine (7.67 g, 63 mmol) and benzyloxycarbonyl chloride (7.17 mL, 50 mmol) was added at −30° C. and under $N_2$. The mixture was allowed to warm to −20° C. and stirred overnight. The mixture was diluted with 100 mL of methylene chloride and washed three consecutive times with 100 mL of a 1:1 mixture of aqueous 5% $KH_2PO_4$ and aqueous 1% $K_2HPO_4$. The organic layer was washed once with 150 mL of brine, dried over $Na_2SO_4$, filtered and the filtrate evaporated in vacuo. Chromatography over silica gel ($CH_3CN$: $NH_4OH$; 100:0.5) yielded the title compound in 79% yield.

Step 2: 2'-O-acetyl-4"-O-benzyloxycarbonyl-11,12-O-thionocarbonyl-erythromycin-6,9-hemiketal (17-2)

2"-O-acetyl-11-O-benzyloxycarbonylerythromycin A (250 mg, 0.3 mmol) was dissolved in tetrahydrofuran (5 mL). 1M sodium hexamethyldisilazide (0.6 mL) was added followed by thiophosgene (0.025 mL) at −78° C. A mixture of aqueous 5% $KH_2PO_4$ and aqueous 1% $K_2HPO_4$ (100 mL) was added and the mixture extracted with 150 mL of methylene chloride. The organic extract was washed once with 100 mL of buffer, followed by 100 mL of brine, dried over $Na_2SO_4$, filtered and evaporated in vacuo. Chromatography over silica gel ($CH_2Cl_2$:$CH_3OH$:$NH_4OH$; 95:5:0.5) afforded the title compound in 57% yield.

Step 3: 2'-O-acetyl-8,9-anhydro-4"-O-benzyloxycarbonyl-12-epierythromycin B-6,9-hemiketal (17-3)

2'-O-acetyl-4"-O-benzyloxycarbonyl-11,12-O-thionocarbonylerythromycin-6,9-hemiketal (75 mg, 0.08 mmol) was dissolved in 25 mL of dry toluene and treated with tributyltin hydride as described in Example 1, Step 3 above. Chromatography of the resulting product over silica gel ($CHCl_3$:$CH_3OH$:$NH_4OH$; 95:5:0.5) gave the title product in 50% yield.

Step 4: 8,9-anhydro-4"-O-benzyloxycarbonyl-12-epierythromycin B-6,9-hemiketal (17-4)

The titled compound (93% yield) was prepared, starting from 15 mg (0.017 mmol) of 2'-O-acetyl-4"-O-benzyloxycarbonyl-11,12-O-thionocarbonylerythromycin-6,9-hemiketal, using the procedure described in Example 1, Step 4.

Step 5: 8,9-anhydro-12-epierythromycin B-6,9-hemiketal 8,9-anhydro-4"-O-benzyloxycarbonyl-12-epierythromycin B-6,9-hemiketal (14 mg, 0.016 mmol), prepared as described above, was dissolved in 5 mL of methanol. The mixture was hydrogenated over 10% Pd-C (25 mg) for 1 hour. The mixture was passed through a filter aid, evaporated in vacuo and chromatographed over silica gel ($CHCl_3$:$CH_3OH$:$NH_4OH$; 90:10:1) to afford the title product in 100% yield.

The physical properties of the compounds of the above examples are shown in Table 1, below.

TABLE 1

Physical Characteristics of the Compounds of Examples 1–16

| Example | $^1$H NMR (dPPM) | | | | MS ($M^±$ + 1) | IR ($CM^{-1}$) |
|---|---|---|---|---|---|---|
| | H-3 | H-7'-8" | H-1' | H-1" | | |
| 1 | 4.05 | 2.42 | 4.58 | 5.19 | 700 | |
| 2 | 4.04 | 2.28 | 4.57 | 5.16 | 684 | |
| 3 | 4.06 | 2.42 | 4.53 | 5.18 | 686 | |
| 4 | 4.09 | 2.23 | 4.54 | 5.21 | 714 | |
| 5 | 4.01 | 3.53, 3.64 | 4.68 | 5.19 | 739 FAB: 738 | |
| 6 | 4.04 | 2.42 | 4.55 | 5.14 | 670 | |
| 7 | 4.04 | 2.23 | 4.58 | 5.16 | 698 | |
| 8 | 3.98 | 3.53, 3.64 | 4.72 | 5.17 | 723 FAB: 720 | |
| 9 | 4.20 | 2.27 | 4.44 | 5.30 | 702 | |
| 10 | 4.21 | 2.41 | 4.42 | 5.27 | 688 | |
| 11 | 4.19 | 2.22 | 4.44 | 5.27 | 716 | |
| 12 | 4.13 | 3.50, 3.61 | 4.57 | 5.24 | 741 FAB: 740 | |
| 13 | 4.14 | 2.31 | 4.46 | 5.38 | 702 | |

TABLE 1-continued

Physical Characteristics of the Compounds of Examples 1–16

| Example | $^1$H NMR (dPPM) | | | | MS ($M^±$ + 1) | IR ($CM^{-1}$) |
|---|---|---|---|---|---|---|
| | H-3 | H-7'-8" | H-1' | H-1" | | |
| 14 | 4.14 | 2.42 | 4.44 | 5.30 | 688 | |
| 15 | 4.14 | 2.22 | 4.47 | 5.28 | 716 | |
| 16 | 4.09 | 3.51, 3.60 | 4.57 | 5.28 | 741 FAB: 740 | |
| 17 | 4.11 | 2.23 | 4.47 | 4.90 | 670 | |
| 1-1 | 3.95 | 2.27 | 4.55 | 4.89 | 776 | |
| 1-2 | 3.94 | 2.31 | 4.67 | 5.03 | FAB: 886 | |
| 1-3 | 3.93 | 2.27 | 4.66 | 5.02 | 760 | 2960, 1730, 1680, 1455 |
| 2-1 | 4.01 | 2.27 | 4.56 | 4.90 | 760 | |
| 2-2 | 3.96 | 2.28 | 4.69 | 5.02 | FAB: 870 | |
| 2-3 | 3.96 | 2.27 | 4.67 | 5.02 | 744 | 2960, 1730, 1690, 1455 |
| 2-4 | 4.26 | 2.26 | 4.50 | 5.17 | 786 | 2960, 1795, 1740, 1460 |
| 13-2 | 4.23 | 2.26 | 4.72 | 5.01 | 788 | 2960, 1795, 1740, 1455, 3490 |
| 13:3 | 4.09 | 2.24 | 4.51 | 5.07 | 770 | 2960, 1790, 1745, 1460 |
| 13:4 | 4.15 | 2.28 | 4.44 | 5.08 | 728 | |
| 17-1 | 3.93 | 2.23 | 4.62 | 4.94 | FAB: 910 | |
| 17-2 | 4.01 | 2.23 | 4.78 | 5.01 | FAB: 952 | |
| 17-3 | 4.10 | 2.25 | 4.55 | 4.90 | 876 | |
| 17-4 | 4.05 | 2.24 | 4.50 | 4.95 | 833 | |

EXAMPLE 18

In Vitro Prokinetic and Antibacterial Activities

The compounds of the present invention were tested in vitro for their ability to induce contraction of smooth muscle strips isolated from rabbit small intestine using the following procedure:

Rabbits were sacrificed and 15 cm of duodenum was rapidly removed and placed in ice-cold modified Ringers solution (120 mM sodium chloride, 25 mM sodium bicarbonate, 4.7 mM potassium chloride, 1.25 mM calcium chloride, 1.20 mM magnesium sulfate and 5.6 mM glucose). The longitudinal muscle layer was separated from the circular muscle by blunt dissection and cut into strips of 10×20 mm. Double-folded strips were vertically suspended between two hooks in 10 mL tissue baths with a mechanical preload of 1 g. The upper hook was connected to an isotonic force transducer, and its displacement was recorded on a Grass polygraph. The tissue baths contained modified Ringers solution at 37° C. and were continuously gassed with 95% oxygen/5% carbon dioxide in order to maintain the pH at 7.5.

After a stabilization period of at least 60 minutes, a contractility dose-response series was performed by adding increasing final concentrations of methacholine ($10^{-7}$M, $10^{-6}$M and $10^{-5}$M) in volumes of 100 μL. The bath solutions were replaced at least three times between doses.

After the methacholine dose-response series was completed, a test compound dose response curve was initiated by the same procedure used for the methacholine dose-response series, with at least five concentrations of test compound within the range of $10^{-10}$M to $10^{-4}$M. The tissues were washed repeatedly between doses, and the studies were completed by recording the contractile response to $10^{-5}$M methacholine to ascertain integrity of the muscle preparation. Contractile responses were expressed as percent of maximal contraction. The concentration of test compound which produces half of the maximal contraction ($ED_{50}$ value) and the negative logarithm of the $ED_{50}$ value ($pED_{50}$) were estimated from the dose-response curves. The $pED_{50}$ values are shown in Table 2 in comparison to erythromycin A which is a known gastrointestinal prokinetic agent. From these data it is evident that the compounds of the present invention are potent prokinetic agents.

sirable side effect if prokinetic therapy. Assays were conducted using methodology well-known in the art (the agar dilution method) As illustrated by the data shown in Table 3, below, the compounds were found to have very low antibacterial potency.

TABLE 3

Antibacterial Activity (MIC's) of 4"-Deoxyerythromycins

| Organism | Strain | Example 7 | Example 11 | Example 15 | Erythromycin |
|---|---|---|---|---|---|
| Staphylococcus aureus | ATCC 6538P | 100 | >100 | 100 | 0.1 |
| Staphylococcus aureus | A5177 | 100 | 100 | >100 | 1.56 |
| Staphylococcus aureus | A-5278 | >100 | >100 | >100 | >100 |
| Staphylococcus aureus | 642A | >100 | >100 | >100 | 0.2 |
| Staphylococcus aureus | NCTC 10649 | 100 | 100 | >100 | 0.2 |
| Staphylococcus aureus | CMX 553 | >100 | >100 | >100 | 0.2 |
| Staphylococcus aureus | 1775 | >100 | >100 | >100 | >100 |
| Staphylococcus epidermidis | 3519 | 100 | 100 | 100 | 0.2 |
| Micrococcus luteus | ATCC 9341 | 12.5 | 25 | 25 | 0.02 |
| Micrococcus luteus | ATCC 4698 | 12.5 | 25 | 25 | 0.1 |
| Enterococcus faecium | ATCC 8043 | 50 | 50 | 50 | 0.05 |
| Streptococcus bovis | A5169 | 50 | 50 | 6.2 | 0.02 |
| Streptococcus agalactiae | CMX 508 | 50 | 6.2 | 6.2 | 0.05 |
| Streptococcus pyogenes | EES61 | 50 | 25 | 25 | 0.05 |
| Streptococcus pyogenes | 930 CONST | >100 | 100 | >100 | >100 |
| Streptococcus pyogenes | 2548 INDUC | 50 | 50 | 50 | 6.2 |
| Escherichia coli | JUHL | >100 | >100 | >100 | 50 |
| Escherichia coli | SS | 100 | >100 | 100 | 0.2 |
| Escherichia coli | DC-2 | >100 | >100 | >100 | 50 |
| Escherichia coli | H560 | >100 | >100 | >100 | 25 |
| Escherichia coli | KNK 437 | >100 | >100 | >100 | 50 |
| Enterobacter aerogenes | ATCC 13048 | >100 | >100 | >100 | 100 |
| Klebsiella pneumoniae | ATCC 8045 | >100 | >100 | >100 | 50 |
| Providencia stuartii | CMX 640 | >100 | >100 | >100 | >100 |
| Pseudomonas aeruginosa | BMH10 | >100 | >100 | >100 | 50 |
| Pseudomonas aeruginosa | A5007 | >100 | >100 | >100 | >100 |
| Pseudomonas aeruginosa | K799/WT | >100 | >100 | >100 | 100 |
| Pseudomonas aeruginosa | K799/61 | >100 | >100 | >100 | 3.1 |
| Pseudomonas aeruginosa | DPHD-5263 | >100 | >100 | >100 | 100 |
| Pseudomonas aeruginosa | DPHD-2862 | >100 | >100 | >100 | >100 |
| Pseudomonas cepacia | 2961 | >100 | >100 | >100 | >100 |
| Acinetobacter calcoaceticus | CMX 669 | >100 | >100 | >100 | 6.2 |

TABLE 2

Induction of In Vitro Rabbit Duodenal Smooth Muscle Contraction

| Example Number | $pED_{50}$ (−log M) | Relative Potency |
|---|---|---|
| 1 | 8.41 | 363 |
| 2 | 11.26 | 257,039 |
| 3 | 9.74 | 7,762 |
| 4 | 11.5 | 199,526 |
| 5 | 7.64 | 62 |
| 6 | —[a] | >8000[a] |
| 7 | —[a] | >8000[a] |
| 8 | 7.30 | 28 |
| 10 | 7.75 | 79 |
| 11 | 8.54 | 490 |
| 12 | 7.63 | 60 |
| 13 | 9.78 | 8,511 |
| 14 | 7.15 | 20 |
| 15 | 7.63 | 60 |
| 16 | 7.39 | 35 |
| erythromycin A | 5.85 | 1.0 |

([a] = Endpoints for the compounds of Examples 6 and 7 could not be obtained, due to their extremely high potency.)

Compounds of the invention were next tested for antibacterial potency, such activity being regarded as an unde- It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

We claim:

1. A method of facilitating the placement of diagnostic and therapeutic instrumentation into the proximal small intestine of a human or other mammal comprising administering to such human or mammal a compound of the formula:

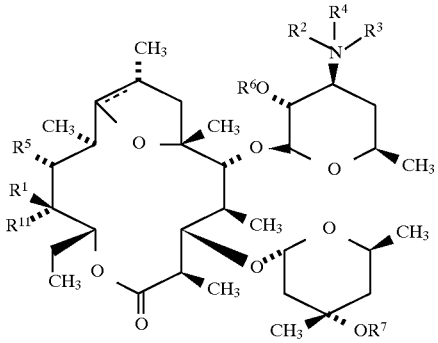

or a pharmaceutically acceptable salt thereof, wherein the dotted line is an optional second C8—to—C9 bond;

(i) one of $R^1$ and $R^{11}$ is hydrogen and the other is methyl, or (ii) $R^{11}$ is methyl and $R^1$ is hydroxy or, taken together with $R^5$ and the carbons to which they are attached, forms a cyclic carbonate;

$R^2$ and $R^3$ are independently selected from the group consisting of:
hydrogen,
loweralkyl,
halo-substituted loweralkyl,
cyano-substituted loweralkyl,
hydroxy-substituted loweralkyl,
amino-substituted loweralkyl,
loweralkenyl,
loweralkynyl,
lower cycloalkyl,
lower cycloalkylmethyl, and
benzyl;
or, taken together, $R^2$ and $R^3$ are —(CH$_2$)n— where n is two to six, so as to form, with the nitrogen to which they are attached, a 3- to 7-membered heterocycle;

$R^4$ is absent or is selected from the group consisting of:
loweralkyl,
loweralkenyl,
loweralkynyl, and
benzyl,
and, when present, is accompanied by a pharmaceutically acceptable counterion so as to form a quaternary ammonium salt;

$R^5$ is selected from the group consisting of hydroxy and —OR$^9$, wherein R$^9$ is selected from the group consisting of:
lower alkyl,
loweralkanoyl, and
—S(O)$_2$CH$_3$; or, taken together with $R^1$ and the carbons to which they are attached, forms a cyclic carbonate;

$R^6$ is selected from the group consisting of hydrogen and loweralkyl; and $R^7$ is selected from the group consisting of hydrogen and methyl; in an amount effective for enhancing gastrointestinal motility.

2. The method according to claim 1, wherein $R^1$ in the compound is hydrogen.

3. The method according to claim 1, wherein at least one of $R^2$ and $R^3$ in the compound is selected from the group consisting of (i) hydrogen and (ii) loweralkyl other than methyl.

4. The method according to claim 2 wherein $R^4$ in the compound is absent.

5. The method according to claim 2 wherein $R^5$ in the compound is hydroxy.

6. The method according to claim 2 wherein $R^6$ in the compound is hydrogen.

7. The method according to claim 2 wherein $R^7$ in the compound is methyl.

8. The method according to claim 2 wherein $R^5$ in the compound is hydroxy, $R^6$ is hydrogen, and $R^7$ is methyl.

9. The method according to claim 1, wherein the compound is selected from the group consisting of:

8,9-anhydro-4"-deoxyerythromycin B-6,9-hemiketal;

8,9-anhydro-4"-deoxy-3'-N-desmethylerythromycin A-6,9-hemiketal;

8,9-anhydro-4"-deoxy-3'-N-desmethyl-3'-N-ethylerythromycin A-6,9-hemiketal;

8,9-anhydro-4"-deoxy-3'-N-desmethylerythromycin B-6,9-hemiketal;

8,9-anhydro-4"-deoxy-3'-N-desmethyl-3'-N-ethylerythromycin B-6,9-hemiketal;

9-deoxo-4",6-dideoxy-8-epi-6,9 epoxyerythromycin A;

9-deoxo-4",6-dideoxy-6,9 epoxyerythromycin A;

9-deoxo-3'-N-desmethyl-4",6-dideoxy-8-epi-6,9-epoxyerythromycin A;

9-deoxo-3'-N-desmethyl-4",6-dideoxy-6,9-epoxyerythromycin A;

9-deoxo-3'-N-desmethyl-4",6-dideoxy-6,9-epoxy-3'-N-ethylerythromycin A; and 9-deoxo-4",6-dideoxy-8-epi-6,9-epoxyerythromycin B.

* * * * *